(12) United States Patent
Li

(10) Patent No.: US 9,907,974 B2
(45) Date of Patent: Mar. 6, 2018

(54) WOUND CARE APPARATUS

(75) Inventor: Yaolin Li, Guangdong (CN)

(73) Assignee: ADVANCE TECHNOLOGY LIMITED, Guangdong (CN)

(*) Notice: Subject to any disclaimer, the term of this patent is extended or adjusted under 35 U.S.C. 154(b) by 339 days.

(21) Appl. No.: 14/113,263

(22) PCT Filed: Sep. 9, 2011

(86) PCT No.: PCT/CN2011/079519
§ 371 (c)(1),
(2), (4) Date: Oct. 22, 2013

(87) PCT Pub. No.: WO2012/079394
PCT Pub. Date: Jun. 21, 2012

(65) Prior Publication Data
US 2014/0088489 A1    Mar. 27, 2014

(30) Foreign Application Priority Data
Dec. 14, 2010 (CN) .......................... 2010 1 0587117

(51) Int. Cl.
*A61M 1/00* (2006.01)
*A61M 27/00* (2006.01)
(Continued)

(52) U.S. Cl.
CPC ......... *A61N 5/0613* (2013.01); *A61M 1/0023* (2013.01); *A61M 1/0058* (2013.01); *A61M 1/0001* (2013.01); *A61M 1/0088* (2013.01); *A61M 2205/051* (2013.01); *A61N 2005/067* (2013.01); *A61N 2005/0643* (2013.01)

(58) Field of Classification Search
CPC .............. A61M 1/0001; A61M 1/0023; A61M 1/0058; A61M 1/0088; A61M 2205/051; A61M 1/0013; A61M 1/0031; A61M 1/0066; A61M 1/008; A61M 1/0084; A61M 2205/052; A61N 2005/0645;
(Continued)

(56) References Cited

U.S. PATENT DOCUMENTS 5,474,528 A * 12/1995 Meserol ................. A61N 5/062
604/20
5,505,726 A * 4/1996 Meserol ............... A61K 9/0009
604/20
(Continued)

*Primary Examiner* — Adam Marcetich
(74) *Attorney, Agent, or Firm* — Jackson IPG PLLC; Demian K. Jackson

(57) ABSTRACT

The invention is applicable to the field of medical care products, and provides a wound care apparatus. The wound care apparatus comprises a pump and a sealed dressing connected to the pump via a first pipeline, a laser being disposed at the upper end of the sealed dressing. The wound care apparatus further comprises a pus bottle that is connected with a piece of sponge and the pump via rubber hoses, respectively. In the invention, the pump of the wound care apparatus is connected with the sealed dressing via the first pipeline, after the wound is dressed by the sealed dressing, the pump is controlled to pump the wounded area into a vacuum state, and ulceration caused by airborne bacterial infection is thus prevented. More importantly, the wound healing rate under a near-negative pressure environment is two to three times of that under normal environment.

2 Claims, 1 Drawing Sheet

(51) Int. Cl.
*A61N 5/06* (2006.01)
*A61N 5/067* (2006.01)

(58) Field of Classification Search
CPC .... A61N 2005/0649; A61N 2005/0659; A61N 2005/066; A61N 2005/067
See application file for complete search history.

(56) References Cited

U.S. PATENT DOCUMENTS

| | | | | |
|---|---|---|---|---|
| 6,231,593 | B1* | 5/2001 | Meserol | A61K 9/0009 604/20 |
| 2002/0120185 | A1* | 8/2002 | Johnson | A61B 5/14542 600/364 |
| 2002/0169442 | A1* | 11/2002 | Neev | A61B 18/203 606/9 |
| 2004/0044384 | A1* | 3/2004 | Leber | A61N 5/0619 607/88 |
| 2004/0073151 | A1* | 4/2004 | Weston | A61F 15/008 602/41 |
| 2005/0137539 | A1* | 6/2005 | Biggie | A61M 1/0096 604/313 |
| 2005/0203452 | A1* | 9/2005 | Weston | A61M 1/0088 602/13 |
| 2006/0079852 | A1* | 4/2006 | Bubb | A61F 13/0203 604/317 |
| 2006/0100594 | A1* | 5/2006 | Adams | A61M 1/0088 604/313 |
| 2006/0155260 | A1* | 7/2006 | Blott et al. | A61M 27/00 |
| 2006/0259102 | A1* | 11/2006 | Slatkine | A61B 17/205 607/88 |
| 2007/0129707 | A1* | 6/2007 | Blott et al. | A61M 27/00 |
| 2007/0208395 | A1* | 9/2007 | Leclerc et al. | A61N 5/06 |
| 2007/0208404 | A1* | 9/2007 | Jones | A61N 1/36021 607/148 |
| 2007/0233208 | A1* | 10/2007 | Kurtz et al. | A61N 5/06 |
| 2007/0239232 | A1* | 10/2007 | Kurtz et al. | A61H 33/00 |
| 2007/0260226 | A1* | 11/2007 | Jaeb | A61M 1/0005 604/543 |
| 2008/0167631 | A1* | 7/2008 | Greer | A61F 13/0203 604/290 |
| 2008/0215019 | A1* | 9/2008 | Malamutmann | A61M 1/0058 604/305 |
| 2008/0215020 | A1* | 9/2008 | Reeves et al. | A61M 1/00 |
| 2009/0177051 | A1* | 7/2009 | Arons et al. | A61F 13/00 |
| 2009/0222023 | A1* | 9/2009 | Boone, III | A61B 17/545 606/131 |
| 2009/0254155 | A1* | 10/2009 | Kanarsky et al. | A61N 1/00 |
| 2009/0264838 | A1* | 10/2009 | Livne et al. | A61F 13/02 |
| 2009/0270820 | A1* | 10/2009 | Johnson | A61M 1/0088 604/290 |
| 2010/0121252 | A1* | 5/2010 | Keltner et al. | A61M 35/00 |
| 2011/0060266 | A1* | 3/2011 | Streeter et al. | A61N 5/06 |
| 2011/0066213 | A1* | 3/2011 | Huttermann et al. | A61N 5/067 |
| 2011/0144410 | A1* | 6/2011 | Kennedy | A61K 31/327 600/2 |
| 2011/0295162 | A1* | 12/2011 | Chang | A61H 9/0057 601/6 |
| 2012/0253432 | A1* | 10/2012 | Loveland | A61N 5/06 |

\* cited by examiner

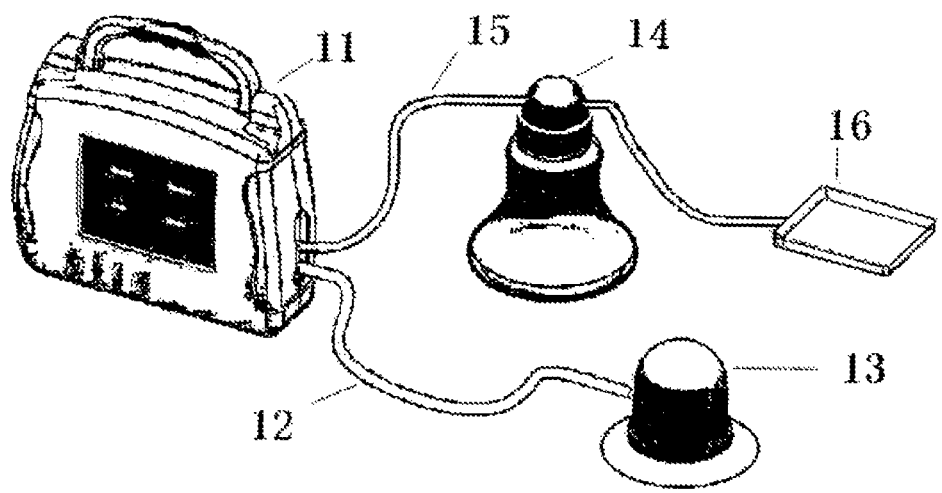

WOUND CARE APPARATUS

FIELD OF THE INVENTION

The invention belongs to the field of medical care products, particularly relates to a wound care apparatus.

BACKGROUND OF THE INVENTION

Skin wounds, for example cuts, burns and scalds, are common. For diabetics and paralyzed people, large-area skin ulcer is likely to appear.

At present, wounds are mainly treated by patches. The therapeutic effect by such treatment manner is not satisfactory, and the healing situations of the wounded area cannot be observed in real time. Furthermore, instant treatment cannot be performed for abnormal situations such as wound bleeding, thus medical accidents are likely to occur. In addition, the freshly healed wounds may be torn when the patches are torn off.

SUMMARY OF THE INVENTION

The purpose of an embodiment of the invention is to provide a wound care apparatus, aimed at solving the problems in wound treatment by patches that the therapeutic effect is not satisfactory, the healing situations of the wounded area cannot be observed in real time, and instant treatment cannot be performed for abnormal situations such as wound bleeding, thus medical accidents are likely to occur.

The embodiment of the invention is accomplished as follows. A wound care apparatus is provided, comprising: a pump and a sealed dressing connected to the pump via a first pipeline, a laser being disposed at the upper end of the sealed dressing, the wound care apparatus further comprising a pus bottle that is connected with a piece of sponge and the pump via rubber hoses, respectively.

Further, the sealed dressing is made of transparent materials.

Further, the transparent materials refer to transparent plastics.

Further, the wavelength of laser light emitted by the laser is 620 nm-655 nm.

Further, the wound care apparatus further comprises a vial to which the pump is connected via a pipeline.

In the embodiment of the invention, the pump of the wound care apparatus is connected with the sealed dressing via the first pipeline, after the wound is dressed by the sealed dressing, the pump is controlled to pump the wounded area into a vacuum state, and ulceration caused by airborne bacterial infection is thus prevented. More importantly, the wound healing rate under a near-negative pressure environment is two to three times of that under normal environment. Furthermore, the laser is controlled to emit laser light 620 nm-655 nm in wavelength to irradiate the wounds, so that the wounds may heal more quickly. A perspective sealed dressing is adopted such that the healing situations of the wounds may be observed in real time, so the treatment on abnormal situations is facilitated. As the pump is connected to the vial via a pipeline, liquid medicine may be pumped to the wounds to promote wound healing. With a rational structure design, pus will not flow through the pump. After use, juts the rubber hoses, the sponge and the sealed dressing are discarded, so sanitary and clean effects are achieved; furthermore, the disposable cost is low. In this way, the invention solves the problems in wound treatment by patches that the therapeutic effect is not satisfactory, the healing situations of the wounded area cannot be observed in real time, and instant treatment cannot be performed for abnormal situations such as wound bleeding, thus medical accidents are likely to occur.

BRIEF DESCRIPTION OF THE DRAWINGS

FIG. 1 is a structure diagram of a wound care apparatus provided in an embodiment of the invention.

DETAILED DESCRIPTION OF THE INVENTION

To make the purposes, technical solutions and advantages of the invention more clear, the invention will be further described in details as below by an embodiment with reference to drawings. It should be understood that, the specific embodiment described herein is just used for explaining the invention, but for limiting the invention.

FIG. 1 shows a structure of a wound care apparatus provided by an embodiment of the invention. The wound care apparatus comprises a pump 11 and a sealed dressing 13 connected to the pump 11 via a first pipeline 12, a laser (not shown) being disposed at the upper end of the sealed dressing 13. The wound care apparatus further comprises a pus bottle 14 that is connected with a piece of sponge 16 and the pump 11 via rubber hoses 15, respectively.

To conveniently observe the healing situations of the wounds in real time, as an embodiment of the invention, the sealed dressing 13 is made of transparent materials, for example, transparent plastics.

When the wound care apparatus is used, the pus bottle 14 is first connected to the pump 11, the sponge 16 is placed on the wounded area, and dirt such as pus and blood in the wounded area is pumped into the pus bottle 14 via a pipeline under the suction of the pump 11.

Then, the wound is dressed by the sealed dressing 13, and the pump 11 is controlled to pump the wounded area in controllable and adjustable conditions into a vacuum state; furthermore, the laser is controlled to emit laser light 620 nm-655 nm in wavelength to irradiate the wounds, so that the wounds may heal more quickly.

As an embodiment of the invention, the wound care apparatus further comprises a vial (not shown) to which the pump 11 is further connected via a pipeline (not shown). The pump 11 pumps liquid medicine to the wounded area from the vial.

In conclusion, the pump is connected with the sealed dressing via the first pipeline, after the wound is dressed by the sealed dressing, the pump is controlled to pump the wounded area into a vacuum state, and ulceration caused by airborne bacterial infection is thus prevented. More importantly, the wound healing rate under a near-negative pressure environment is two to three times of that under normal environment.

Furthermore, the laser is controlled to emit laser light 620 nm-655 nm in wavelength to irradiate the wounds, so that the wounds may heal more quickly.

A perspective sealed dressing is adopted such that the healing situations of the wounds may be observed in real time, so the treatment on abnormal situations is facilitated. As the pump is connected to the vial via a pipeline, liquid medicine may be pumped to the wounds to promote wound healing.

With a rational structure design, pus will not flow through the pump. After use, juts the rubber hoses, the sponge and the sealed dressing are discarded, so sanitary and clean effects are achieved; furthermore, the disposable cost is low.

The above contents just describe a preferred embodiment of the invention, and are not used for limiting the invention. Any modifications, equivalent replacements and improvements made within the spirit and principle of the invention should fall into the protection scope of the invention.

What is claimed is:

1. A wound care apparatus, comprising:
   a pump;
   a sponge;
   a sealed dressing made of transparent plastics and connected to the pump via a first pipeline such that the pump is capable of creating a vacuum state at a wound under the sealed dressing, absent the sponge,
   a laser disposed at the upper end of the sealed dressing so as to irradiate the wound,
   a vial to which the pump is connected via a second pipeline so as to pump liquid medicine to the wound, and
   a pus bottle connected between the sponge and the pump via rubber hoses such that debris from the wound is capable of being drawn by the pump from the sponge into the pus bottle absent the sealed dressing.

2. The wound care apparatus according to claim 1, wherein the wavelength of laser light emitted by the laser is 620 nm-655 nm.

* * * * *